United States Patent [19]

Ono et al.

[11] 4,303,664
[45] Dec. 1, 1981

[54] NOVEL PENICILLIN DERIVATIVES CONTAINING A COUMARIN NUCLEUS AND MEDICINES CONTAINING THE SAME

[75] Inventors: Syoji Ono, Kodaira; Takashi Sugiyama, Tokyo; Yoshiko Kawakami, Higashiyamato; Yataro Ichikawa, Fuchu; Yoji Suzuki; Hitoshi Ohmori, both of Hino; Akiko Azuma, Kodaira, all of Japan

[73] Assignee: Teijin Limited, Osaka, Japan

[21] Appl. No.: 884,509

[22] Filed: Mar. 8, 1978

[51] Int. Cl.³ .................... A61K 31/43; C07D 499/68
[52] U.S. Cl. .................................. 424/271; 260/239.1
[58] Field of Search ...................... 260/239.1; 424/271

[56] References Cited
U.S. PATENT DOCUMENTS

| | | | |
|---|---|---|---|
| 3,433,784 | 3/1969 | Long et al. ........................ | 260/239.1 |
| 3,939,150 | 2/1976 | Murakami et al. ............... | 260/239.1 |
| 3,951,952 | 4/1976 | Hamanaka et al. .............. | 260/239.1 |
| 3,954,734 | 5/1976 | Doub et al. ....................... | 260/239.1 |
| 4,005,075 | 1/1977 | Yamada et al. ................... | 260/239.1 |

Primary Examiner—Natalie Trousof
Assistant Examiner—Vera C. Clarke
Attorney, Agent, or Firm—Sughrue, Mion, Zinn, Macpeak and Seas

[57] ABSTRACT

This invention provides novel penicillin derivatives of formula [I];

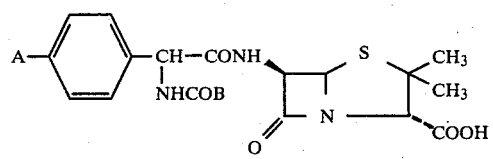

wherein A is hydrogen or hydroxyl, and B represents the cumarin nucleus of formula [III-a];

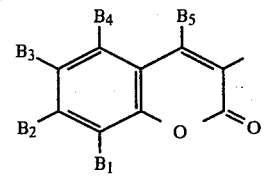

in which $B_1$, $B_2$, $B_3$, $B_4$ and $B_5$ are same or different, and are hydrogen or substituent groups that may contain nitrogen, sulfur or oxygen atom, or nontoxic salts thereof, and bactericides containing said novel penicillin derivatives or nontoxic salts thereof as the main ingredient, and also an advantageous process for producing said novel penicillin derivatives or nontoxic salts thereof, which comprises reacting a derivative of α-aminobenzylpenicillin with a coumarincarboxylic acid or reacting 6-aminopencillanic acid, a carboxylic acid salt thereof or a protected derivative thereof having the carboxyl blocked with a readily removable protecting group, with a coumarincarboxylic acid phenylglycinamide.

6 Claims, No Drawings

NOVEL PENICILLIN DERIVATIVES CONTAINING A COUMARIN NUCLEUS AND MEDICINES CONTAINING THE SAME

The object of this invention is to provide novel penicillin derivatives and nontoxic salts thereof. A further object of this invention is to provide bactericides containing novel penicillin derivatives or nontoxic salts thereof as the main ingredient. A still further object of this invention is to provide advantageous processes for industrial production of novel penicillin derivatives or nontoxic salts thereof.

This invention relates to novel penicillin derivatives of formula [I]

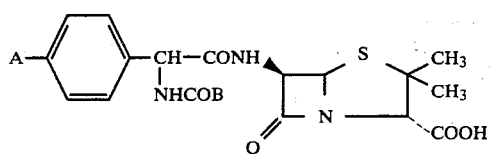

wherein A is hydrogen or hydroxyl, and B represents the coumarin nucllus of formula [III-a]

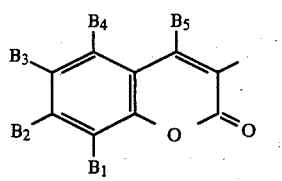

in which $B_1$, $B_2$, $B_3$, $B_4$ and $B_5$ are same or different and are hydrogen or substituent groups which may contain nitrogen, sulfur, or oxygen atom, or nontoxic salts thereof, and relates to bactericides containing as the main ingredient said novel penicillin derivatives or nontoxic salts thereof. This invention also relates to advantageous processes for industrial production of said novel penicillin derivatives and nontoxic salts thereof, which comprises reacting a derivative of α-aminobenzylpenicillin of formula [II]

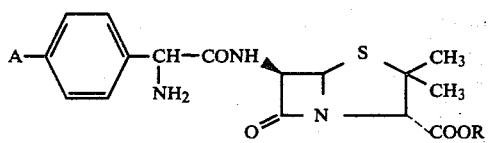

wherein A is hydrogen or hydroxyl, and R is hydrogen, a salt-forming cation, or a readily removable protecting group, with a coumarincarboxylic acid of formula [III]

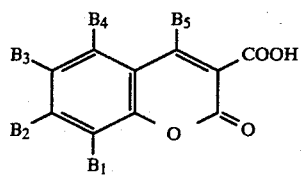

wherein $B_1$, $B_2$, $B_3$, $B_4$ and $B_5$ are same or different, and are hydrogen or substituent groups which may contain nitrogen, sulfur or oxygen atom, or a reactive carboxylic acid derivative thereof, or reacting 6-aminopenicillanic acid, a carboxylic acid salt thereof or a protected derivative thereof having the carboxyl blocked with a readily removable protecting group, with a coumarincarboxylic acid phenylglycinamide of formula [IV]

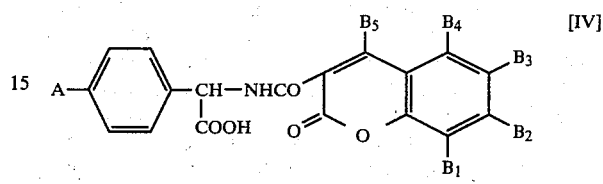

wherein A is hydrogen or hydroxyl, and $B_1$, $B_2$, $B_3$, $B_4$ and $B_5$ are same or different, and are hydrogen or substituent groups which may contain nitrogen, sulfur or oxygen atom, or a reactive carboxylic acid derivative thereof; and then effecting if necessary, salt formation and/or removal of the protecting group.

Such novel penicillin derivatives and nontoxic salts thereof are heretofore unknown. U.S. Pat. No. 3,433,784 described a process for producing penicillins of the formula

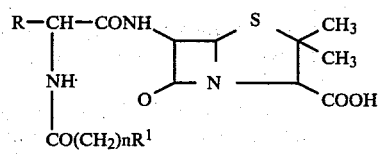

wherein R is phenyl or thienyl; $R^1$ is 2-quinoyl, 4-quinoyl, N-phthalimido, or a specific monocyclic 5- or 6-membered heterocyclic radical; and n is 0 or 1, or nontoxic salts thereof, by the reaction of an aminomethylpenicillin with a reactive derivative of a heterocyclic carboxylic acid. However, no description can be found in the specification of that patent about compounds in which $R^1$ in the above formula is a coumarin nucleus. Although there is cited in the above patent only one radical expressed by the formula

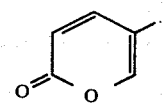

as the example of lactone rings, the bactericidal activity of this type of compounds is not completely satisfactory, the minimum inhibition concentration against *Pseudomonas aeruginosa*, a kind of gram-negative bacteria, being 500 μg/ml.

This invention provides novel penicillin derivatives and nontoxic salts thereof, and more particularly provides those represented by formula [I] and nontoxic salts thereof having exceptionally prominent bactericidal activities.

In the formula [I] shown above, A represents hydrogen or hydroxyl, and B denotes the coumarin nucleus represented by formula [III-a] in which $B_1, B_2, B_3, B_4$ and $B_5$ are hydrogen or substituent groups which may contain nitrogen, sulfur or oxygen atom. By such substituent group is herein meant any group which is usually considered capable of replacing hydrogen atoms on an aromatic nucleus.

Further, the more preferable examples of novel penicillin derivatives and nontoxic salts thereof of this invention are those in which substituent groups $B_1$, $B_2$, $B_3$, $B_4$ and $B_5$ on the coumarin nucleus in formula [I] are selected from the group consisting of hydroxyl, thiol, alkoxyl of 1 to 4 carbon atoms, alkylmercapto of 1 to 4 carbon atoms, acyl or acyloxy of 1 to 10 carbon atoms, amino, alkylamino of 1 to 8 carbon atoms, acylamino of 1 to 10 carbon atoms, nitro, alkyl of 1 to 4 carbon atoms, halogen, carboxyl, alkoxycarbonyl of 2 to 5 carbon atoms, and carboxyl nontoxic salt; and the most preferable examples are those in which at least $B_1$ or $B_3$ of the substituent groups $B_1$, $B_2$, $B_3$, $B_4$ and $B_5$ are substituent groups other than hydrogen. As preferred examples of said substituent groups on the coumarin nucleus may be mentioned, among others, hydroxyl, thiol, alkoxyl of 1 to 4 carbon atoms such as methoxy, ethoxy, propoxy, and butoxy; alkylmercapto of 1 to 4 carbon atoms such as methylmercapto, ethylmercapto, propylmercapto, and butylmercapto; acyl of 1 to 10 carbon atoms such as formyl, acetyl, propionyl, butyryl, caproyl, caprylyl, and decanoyl; and acyloxy derived therefrom; amino, alkylamino of 1 to 8 carbon atoms such as methylamino, dimethylamino, ethylamino, diethylamino, propylamino, dipropylamino, butylamino, dibutylamino, and octylamino; acylamino having acyl group as stated above; nitro, alkyl of 1 to 4 carbon atoms such as methyl, ethyl, propyl, and butyl; halogen such as chloro and bromo; carboxyl, nontoxic salt thereof such as salt of sodium, potassium, and calcium; and alkoxycarbonyl of 2 to 5 carbon atoms such as methoxycarbonyl, ethoxycarbonyl, propoxycarbonyl, and butoxycarbonyl.

Examples of the nontoxic salts of the novel penicillin derivatives described above may include, among others, nontoxic salts of metals such as sodium, potassium, and calcium, salts of ammonium, and salts of substituted ammonium such as salts of diethylamine, triethylamine, and procaine.

Novel penicillin derivatives provided by this invention and represented by formula [I] are typified by:

(100) α-(coumarin-3-carbonamido)benzylpenicillin
(102) α-(8-hydroxycoumarin-3-carbonamido)benzylpenicillin
(104) α-(7-hydroxycoumarin-3-carbonamido)benzylpenicillin
(106) α-(6-hydroxycoumarin-3-carbonamido)benzylpenicillin
(108) α-(5-hydroxycoumarin-3-carbonamido)benzylpenicillin
(110) α-(8-mercaptocoumarin-3-carbonamido)benzylpenicillin
(112) α-(6-mercaptocoumarin-3-carbonamido)benzylpenicillin
(114) α-(8-methoxycoumarin-3-carbonamido)benzylpenicillin
(116) α-(7-methoxycoumarin-3-carbonamido)benzylpenicillin
(118) α-(6-methyoxycoumarin-3-carbonamido)benzylpenicillin
(120) α-(8-ethoxycoumarin-3-carbonamido)benzylpenicillin
(122) α-(6-ethoxycoumarin-3-carbonamido)benzylpenicillin
(124) α-(8-propoxycoumarin-3-carbonamido)benzylpenicillin
(126) α-(8-butoxycoumarin-3-carbonamido)benzylpenicillin
(128) α-(8-methylmercaptocoumarin-3-carbonamido)benzylpenicillin
(130) α-(6-ethylmercaptocoumarin-3-carbonamido)benzylpenicillin
(132) α-(6-propylmercaptocoumarin-3-carbonamido)benzylpenicillin
(134) α-(8-butylmercaptocoumarin-3-carbonamido)benzylpenicillin
(136) α-(6-formylcoumarin-3-carbonamido)benzylpenicillin
(138) α-(8-acetylcoumarin-3-carbonamido)benzylpenicillin
(140) α-(8-propionylcoumarin-3-carbonamido)benzylpenicillin
(142) α-(8-butyrylcoumarin-3-carbonamido)benzylpenicillin
(144) α-(8-caproylcoumarin-3-carbonamido)benzylpenicillin
(146) α-(8-caprylylcoumarin-3-carbonamido)benzylpenicillin
(148) α-(8-decanoylcoumarin-3-carbonamido)benzylpenicillin
(150) α-(8-acetoxycoumarin-3-carbonamido)benzylpenicillin
(152) α-(7-acetoxycoumarin-3-carbonamido)benzylpenicillin
(154) α-(6-acetoxycoumarin-3-carbonamido)benzylpenicillin
(156) α-(5-acetoxycoumarin-3-carbonamido)benzylpenicillin
(158) α-(8-decanoyloxycoumarin-3-carbonamido)benzylpenicillin
(160) α-(8-aminocoumarin-3-carbonamido)benzylpenicillin
(162) α-(6-aminocoumarin-3-carbonamido)benzylpenicillin
(164) α-(6-methylaminocoumarin-3-carbonamido)benzylpenicillin
(166) α-(6-ethylaminocoumarin-3-carbonamido)benzylpenicillin
(168) α-(6-diethylaminocoumarin-3-carbonamido)benzylpenicillin
(170) α-(8-propylaminocoumarin-3-carbonamido)benzylpenicillin
(172) α-(8-dibutylaminocoumarin-3-carbonamido)benzylpenicillin
(174) α-(6-octylaminocoumarin-3-carbonamido)benzylpenicillin
(176) α-(6-acetylaminocoumarin-3-carbonamido)benzylpenicillin
(178) α-(6-caprylylaminocoumarin-3-carbonamido)benzylpenicillin
(180) α-(8-nitrocoumarin-3-carbonamido)benzylpenicillin
(182) α-(6-nitrocoumarin-3-carbonamido)benzylpenicillin
(184) α-(4-methylcoumarin-3-carbonamido)benzylpenicillin (186) α-(6-methylcoumarin-3-carbonamido)benzylpenicillin
(188) α-(8-methylcoumarin-3-carbonamido)benzylpenicillin
(190) α-(6-ethylcoumarin-3-carbonamido)benzylpenicillin
(192) α-(8-propylcoumarin-3-carbonamido)benzylpenicillin
(194) α-(8-butylcoumarin-3-carbonamido)benzylpenicillin
(196) α-(6-chlorocoumarin-3-carbonamido)benzylpenicillin
(198) α-(6-bromocoumarin-3-carbonamido)benzylpenicillin
(200) α-(8-carboxycoumarin-3-carbonamido)benzylpenicillin
(202) α-(6-carboxycoumarin-3-carbonamido)benzylpenicillin
(204) α-(8-methoxycarbonylcoumarin-3-carbonamido)benzylpenicillin
(206) α-(8-ethoxycarbonylcoumarin-3-carbonamido)benzylpenicillin
(208) α-(8-butoxycarbonylcoumarin-3-carbonamido)benzylpenicillin
(210) α-(4,6-dimethylcoumarin-3-carbonamido)benzylpenicillin
(212) α-(6,8-dibromocoumarin-3-carbonamido)benzylpenicillin
(214) α-(6,8-dichlorocoumarin-3-carbonamido)benzylpenicillin
(216) α-(5,7-dimethoxycoumarin-3-carbonamido)benzylpenicillin
(218) α-(8-methoxy-4-nitrocoumarin-3-carbonamido)benzylpenicillin
(220) α-(7-chloro-8-methoxycoumarin-3-carbonamido)benzylpenicillin
(222) α-(4,6,8-triethylcoumarin-3-carbonamido)benzylpenicillin
(224) α-(6-acetylamino-7-hydroxy-4,8-dimethylcoumarin-3-carbonamido)benzylpenicillin
(226) α-(7,8-dihydroxy-4,5,6-trimethylcoumarin-3-carbonamido)benzylpenicillin
(228) α-(coumarin-3-carbonamido)-p-hydroxybenzylpenicillin
(230) α-(8-hydroxycoumarin-3-carbonamido)-p-hydroxybenzylpenicillin
(232) α-(7-hydroxycoumarin-3-carbonamido)-p-hydroxybenzylpenicillin
(234) α-(6-hydroxycoumarin-3-carbonamido)-p-hydroxybenzylpenicillin
(236) α-(8-methoxycoumarin-3-carbonamido)-p-hydroxybenzylpenicillin
(238) α-(6-methoxycoumarin-3-carbonamido)-p-hydroxybenzylpenicillin
(240) α-(8-ethoxycoumarin-3-carbonamido)-p-hydroxybenzylpenicillin
(242) α-(6-propoxycoumarin-3-carbonamido)-p-hydroxybenzylpenicillin
(244) α-(8-ethylmercaptocoumarin-3-carbonamido)-p-hydroxybenzylpenicillin
(246) α-(6-acetylcoumarin-3-carbonamido)-p-hydroxybenzylpenicillin
(248) α-(8-caproylcoumarin-3-carbonamido)-p-hydroxybenzylpenicillin
(250) α-(8-acetoxycoumarin-3-carbonamido)-p-hydroxybenzylpenicillin
(252) α-(6-acetoxycoumarin-3-carbonamido)-p-hydroxybenzylpenicillin
(254) α-(8-diethylaminocoumarin-3-carbonamido)-p-hydroxybenzylpenicillin
(256) α-(6-butylaminocoumarin-3-carbonamido)-p-hydroxybenzylpenicillin
(258) α-(4-methylcoumarin-3-carbonamido)-p-hydroxybenzylpenicillin
(260) α-(6-methylcoumarin-3-carbonamido)-p-hydroxybenzylpenicillin
(262) α-(6-ethylcoumarin-3-carbonamido)-p-hydroxybenzylpenicillin
(264) α-(8-propylcoumarin-3-carbonamido)-p-hydroxybenzylpenicillin
(266) α-(6-chlorocoumarin-3-carbonamido)-p-hydroxybenzylpenicillin
(268) α-(8-methoxycarbonylcoumarin-3-carbonamido)-p-hydroxybenzylpenicillin
(270) α-(8-ethoxycarbonylcoumarin-3-carbonamido)-p-hydroxybenzylpenicillin
(272) α-(4,6-dimethylcoumarin-3-carbonamido)-p-hydroxybenzylpenicillin
(274) α-(6,8-dichlorocoumarin-3-carbonamido)-p-hydroxylbenzylpenicillin
(276) α-(5,7-diethoxycoumarin-3-carbonamido)-p-hydroxybenzylpenicillin
(278) α-(8-propoxy-4-nitrocoumarin-3-carbonamido)-p-hydroxybenzylpenicillin
(280) α-(7-chloro-8-methoxycoumarin-3-carbonamido)-p-hydroxybenzylpenicillin
(282) α-(8-hydroxycoumarin-3-carbonamido)benzylpenicillin sodium salt
(284) α-(8-ethoxycoumarin-3-carbonamido)benzylpenicillin sodium salt
(286) α-(6-methylcoumarin-3-carbonamido)-p-hydroxybenzylpenicillin triethylammonium salt
(288) α-(4,6-diethylcoumarin-3-carbonamido)benzylpenicillin procaine salt These novel penicillin derivatives may be advantageously produced on an industrial scale, for example, by either one of the two processes described below. In the first process the objective compounds can be prepared by the reaction of an α-aminobenzylpenicillin with a coumarincarboxylic acid or a reactive derivative thereof. The α-aminobenzylpenicillins used as the starting material are compounds represented by formula [II], in which A is hydrogen or hydroxyl, and R is hydrogen or a protecting group including alkali metals such as sodium and potassium, alkaline earth metals such as magnesium and calcium, salt-forming cations such as ammonium, cations of tertiary amines such as trimethylamine, triethylamine, tributylamine, pyridine, N-methylpiperidine and N-methylmorpholine, a trialkylsilyl radical of 1 to 4 carbon atoms such as trimethylsilyl and t-butyldimethylsilyl, or a radical capable of forming a reactive ester such as cyanomethyl, methoxymethyl, p-nitrophenyl, trichlorophenyl, pentachlorophenyl, p-nitrophenylthio, tetrahydropyranyl, succinimido, and phthalimido. Such reactive esters are obtainable, for example, by reacting an α-aminobenzylpenicillin of formula [II] in which R is hydrogen with the corresponding alcohol or thioalcohol in the presence of a condensing agent such as dicyclohexylcarbodiimide.

By the coumarincarboxylic acids or reactive carboxylic acid derivatives thereof are meant those compounds represented by formula [III] or reactive carboxylic acid derivatives thereof which include acid halides such as acid chlorides; monomethylcarbonate; mixed acid anhydrides thereof with other carboxylic acids such as pivalic acid; or reactive esters thereof; reactive amides such as N-acylsaccharines, N-acylbenzoylamides, N,N'-dichlorohexyl-N-acylureas and N-acylsulfonamides; or reactive cyanides.

It is preferred to carry out the reaction of α-aminobenzylpenicillin with coumarincarboxylic acid in an inert solvent in the presence or absence of a basic substance at a temperature of from −50° C. to 80° C., preferably from −40° C. to 30° C. About three hours, at the longest, are sufficient for the completion of the reaction. As the solvent may be used, among others, water, acetone, tetrahydrofuran, dioxane, acetonitrile, dimethylformamide, methanol, ethanol, methoxyethanol, diethyl ether, isopropyl ether, benzene, toluene, methylene chloride, chloroform, ethyl acetate, methyl isobutyl ketone or a mixture thereof. The preferred basic substance is a basic alkali metal compound such as an alkali hydroxide, e.g., sodium hydroxide, an alkali bicarbonate, e.g., potassium bicarbonate, an alkali carbonate, e.g., sodium carbonate, or an alkali acetate, e.g. sodium acetate; a tertiary amine e.g. trimethylamine, triethylamine, tributylamine, pyridine, N-methylpyridine, N-methylmorpholine, lutidine or collidine; and a secondary amine e.g. dicyclohexylamine.

If a coumarincarboxylic acid containing free carboxyl group is used as the starting material, the reaction is preferably carried out in the presence of a condensing agent such as dicyclohexylcarbodiimide, N-cyclohexyl-N'-morpholinoethylcarbodiimide, N,N'-diethylcarbodiimide, trialkyl phosphites, ethyl polyphosphate, phosphorus oxychloride, phosphorus trichloride and oxalyl chloride.

The second process for producing novel penicillin derivatives and nontoxic salts thereof of this invention involves the reaction of 6-aminopenicillanic acid, a salt of the acid, or a protected derivative thereof having the carboxyl blocked with a readily removable protecting group, with a coumarincarboxylic acid phenylglycinamide of formula [IV] or a reactive carboxylic acid derivative thereof.

As the salt-forming and protecting groups in said salts and protected derivatives of 6-aminopenicillanic acid used as the starting material, may be employed the same groups as those typified as R in formula [II] stated in the first process.

As the reactive derivatives of coumarincarboxylic acid phenylglycinamide may be used the same type of reactive derivatives as those described in reactive derivatives of coumarincarboxylic acid expressed by formula [III]. Such coumarincarboxylic acid phenylglycinamides can be readily prepared by the condensation reaction between the corresponding phenylglycines and the corresponding coumarincarboxylic acids or their reactive carboxylic acid derivatives in a similar manner as in the first process.

As examples of said coumarincarboxylic acid phenylglycinamides of formula [IV] and reactive carboxylic acid derivatives thereof, as can be readily seen from the examples of the objective compounds illustrated hereinbefore, may be cited, among others, N-(coumarin-3-carbonyl)phenylglycine, N-(8-hydroxylcoumarin-3-carbonyl)phenylglycine, N-(6-methylcoumarin-3-carbonyl)phenylglycine, N-(6-chlorocoumarin-3-carbonyl)phenylglycine, N-(coumarin-3-carbonyl)-p-hydroxyphenylglycine, N-(6-hydroxycoumarin-3-carbonyl)-p-hydroxyphenylglycine, N-(8-ethylcoumarin-3-carbonyl)-p-hydroxyphenylglycine, and N-(4,6-dimethylcoumarin-3-carbonyl)-p-hydroxyphenylglycine.

The condensation reaction in the second process can also be effected in the same manner as in the first process.

Thus, it is possible, according to the first or second process, to produce novel penicillin derivatives, salts thereof, or protected derivatives thereof having the carboxyl blocked with a readily removable protecting group, in which the amino group in α-aminobenzylpenicillin has been replaced by a coumarin nucleus. Isolation of the product from the reaction mixture may be accomplished by well-known methods, taking into consideration the type of solvent used and the different modes of reaction due to the type of starting materials. When the isolated product is a protected derivative, it may be converted to free acid by removal of the protecting group through, for example, reduction, or acid or alkaline hydrolysis. The free acid thus obtained may then be converted to a nontoxic salt thereof by well-known methods. The novel penicillin derivatives represented by formula [I] and nontoxic salts thereof can thus be provided according to this invention.

It has been demonstrated by our studies that such novel penicillin derivatives and nontoxic salts thereof exhibit prominent bactericidal activity.

That is, in addition to being active against gram-positive bacteria, they show higher bactericidal activity against gram-negative bacteria than ampicillin, carbenicillin or amoxycillin, which are known to be active against such type of bacteria and are extensively used for this purpose. Particularly, it was found that they exhibit extremely high bactericidal activity against *Pseudomonus aeruginosa,* a kind of gram-negative bacteria.

The bactericides of this invention may be used, for example, by intravenous injection or oral administration usually at a daily dose of about 0.1–5 g.

This invention will be further illustrated by the following examples, which are not to be considered a limitation thereupon in any respect.

EXAMPLE 1

D(−)-α-(Coumarin-3-carbonamido)benzylpenicillin

A mixture of coumarin-3-carboxylic acid (0.19 g) and oxalyl chloride (0.5 g) was heated under reflux for thirty minutes. After the excess oxalyl chloride had been removed under reduced pressure, the remaining powder was suspended in acetone (2 ml).

Sodium ampicillin (0.371 g) was dissolved in a mixture of water (2.5 ml) and acetone (2.5 ml) under cooling on ice. To this solution was added dropwise the above suspension over ten minutes, during which time the pH of the reaction system was held in the range of from 7 to 9 by addition of a dilute aqueous solution of sodium hydroxide. After all the suspension had been added, the mixture was stirred under cooling for thirty minutes, ethyl acetate (10 ml) was added, and the pH was adjusted to 2 with a dilute aqueous solution of hydrochloric acid. The ethyl acetate layer was then separated, washed with a 1 N aqueous hydrochloric acid (5 ml) and a saturated aqueous solution of sodium chloride (5 ml), and dried over anhydrous sodium sulfate. After removal of the solvent the residue was treated with ether, yielding 0.346 g of white powder.

Recrystallization with ethyl acetate gave 0.320 g of white crystals, m.p. 172°–4° C. (dec.).

| Elemental analysis ($C_{26}H_{23}N_3O_7S$): | | | |
|---|---|---|---|
| | C | H | N |
| Observed | 59.67 | 4.20 | 7.85 |
| Calculated | 59.88 | 4.45 | 8.06 |

Infrared spectrum (KBr, $cm^{-1}$):
3250 (NH, OH), 1770 (β-lactam), 1700 (carboxylic acid), 1650 (amide), 1700, 1640, 1560 (lactone)
Nuclear magnetic resonance spectrum ($CDCl_3$ + dimethylsulfoxide (DMSO), δ, ppm):

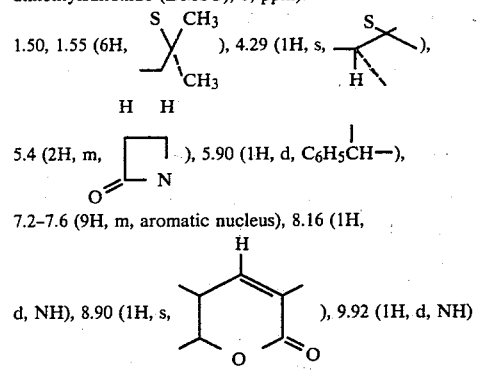

1.50, 1.55 (6H, ... ), 4.29 (1H, s, ... ), 5.4 (2H, m, ... ), 5.90 (1H, d, $C_6H_5CH$—), 7.2–7.6 (9H, m, aromatic nucleus), 8.16 (1H, d, NH), 8.90 (1H, s, ... ), 9.92 (1H, d, NH)

EXAMPLE 2

D(—)-α-(6-Chlorocoumarin-3-carbonamido)benzylpenicillin

A mixture of 6-chlorocoumarin-3-carboxylic acid (0.225 g) and thionyl chloride (0.5 ml) was heated under reflux for thirty minutes. After the excess thionyl chloride had been removed under reduced pressure, the residue was dissolved in acetone. This solution was added dropwise to a solution of sodium ampicillin (0.371 g) in acetone-water (1:1) (5 ml) under cooling on ice, during which time the pH of the liquid was maintained in the range of 7 to 9 by addition of a dilute aqueous solution of sodium hydroxide. After the addition of the acetone solution was completed, the mixture was stirred for thirty minutes, ethyl acetate (10 ml) was added, and the pH was adjusted to 2 with a dilute aqueous solution of hydrochloric acid. The ethyl acetate layer was then separated, washed with a 1 N aqueous hydrochloric acid and a saturated solution of sodium chloride in succession, and dried over anhydrous sodium sulfate. After removal of the solvent under reduced pressure the resulting residue was treated with ether, yielding 0.41 g of white powder melting at 155° C. (dec.).
Elemental analysis ($C_{26}H_{22}N_3O_7SCl$):

| | C | H | N |
|---|---|---|---|
| Observed | 55.82 | 3.78 | 7.21 |
| Calculated | 56.16 | 3.99 | 7.56 |

Infrared spectrum (nujiol, $cm^{-1}$): 3250 (NH), 1765 (β-lactam), 1715 (carboxylic acid), 1640 (amide), 1715, 1640, 1560 (lactone)
Nuclear magnetic resonance spectrum ($CDCl_3$, δ, ppm): 1.50 (6H, s), 4.36 (1H, s), 5.47 (1H, d), 5.6–6.0 (2H, m), 7.3–7.6(8H, m), 8.78 (1H, s), 9.90 (1H, d)

EXAMPLE 3

D(—)-α-(6-Bromocoumarin-3-carbonamido)benzylpenicillin

A mixture of 6-bromocoumarin-3-carboxylic acid (0.269 g) and thionyl chloride (1 ml) was heated under reflux for thirty minutes. After the excess thionyl chloride had been removed under reduced pressure, the remaining residue was dissolved in acetone. This solution was added dropwise under cooling on ice to a solution of sodium ampicillin (0.371 g) in acetone-water (1:1) (5 ml), during which time the pH of the reaction mixture was maintained in the range of from 7 to 9 with a dilute aqueous solution of sodium hydroxide. After the addition was completed, the mixture was stirred for thirty minutes, and treated in the similar manner as in example 2, yielding D(—)-α-(6-bromocoumarin-3-carbonamido)benzylpenicillin (0.22 g), m.p. 138°–9° C. (dec.).
Elemental analysis ($C_{26}H_{23}N_3O_7SBr$):

| | C | H | N |
|---|---|---|---|
| Observed | 51.70 | 3.72 | 6.80 |
| Calculated | 51.96 | 3.69 | 6.99 |

Infrared spectrum (nujiol, $cm^{-1}$): 3300 (NH), 1770 (β-lactam), 1700 (carboxylic acid), 1640 (amide), 1700, 1640, 1550 (lactone)
Nuclear magnetic resonance spectrum ($CDCl_3$, δ, ppm): 1.55, 1.57 (6H, d), 4.37 (1H, s), 5.47 (1H, d), 5.67–5.61 (2H, m), 7.3–7.9 (8H, m), 8.41 (1H, s), 8.82 (1H, d), 9.90 (1H, d)

EXAMPLE 4

D(—)-α-(6,8-Dibromocoumarin-3-carbonamido)benzylpenicillin

The above penicillin derivative (0.182 g), m.p. 174°–6° C. (dec.), was obtained from 6,8-dibromocoumarin-3-carboxylic acid (0.348 g) in the same manner as in example 2.
Elemental analysis ($C_{26}H_{21}N_3O_7SBr_2$):

| | C | H | N |
|---|---|---|---|
| Observed | 45.56 | 3.20 | 5.90 |
| Calculated | 45.92 | 3.11 | 6.18 |

Infrared spectrum (nujiol, $cm^{-1}$): 3300 (NH, OH), 1770 (β-lactam), 1725, 1610, 1550 (lactone), 1650 (amide)
Nuclear magnetic resonance spectrum ($CDCl_3$+DMSO-$d_6$, δ, ppm): 1.53, 1.60 (6H, d), 4.38 (1H, s), 5.49 (1H, d), 5.7–6.1 (2H, m), 7.3–7.9 (7H, m), 8.60 (1H, s), 8.80 (1H, d), 9.70 (1H, d)

EXAMPLE 5

D(—)-α-(4,6-Dimethylcoumarin-3-carbonamido)benzylpenicillin

A mixture of 4,6-dimethylcoumarin-3-carboxylic acid (0.109 g) and thionyl chloride (0.5 ml) was heated under reflux for one hour. After the excess thionyl chloride had been distilled off under reduced pressure, the resulting residue was dissolved in methylene chloride (3 ml). Separately, ampicillin trihydrate (0.202 g) was suspended in methylene chloride (6 ml) and then dissolved by adding 0.101 g of triethylamine. Magnesium sulfate (0.5 g) was added to the solution and the mixture was stirred for twenty minutes. After filtering off the magnesium sulfate, the solution of acid chloride in methylene chloride obtained above was added dropwise to the filtrate under stirring and cooling on ice. After the addition was completed, the mixture was stirred for one hour, ethyl acetate (30 ml) was added, and the pH was adjusted to 2 with a dilute aqueous solution of hydrochloric acid. The organic layer was separated, washed with a dilute aqueous solution of hydrochloric acid and water in succession, and dried over anhydrous sodium sulfate. After removal of the solvent under reduced pressure, the resulting residue was washed with ether and ethyl acetate, affording 0.152 g of D(−)-α-(4,6-dimethylcoumarin-3-carbonamido)benzylpenicillin, m.p. 184°–5° C. (dec.).
Elemental analysis ($C_{28}H_{27}N_3O_7S$):

|  | C | H | N |
|---|---|---|---|
| Observed | 60.59 | 4.65 | 6.85 |
| Calculated | 61.14 | 4.95 | 7.64 |

Infrared spectrum (KBr, cm$^{-1}$): 3350 (NH), 1780 (β-lactam), 1710 (carboxylic acid), 1640 (amide), 1710, 1640, 1575 (lactone)
Nuclear magnetic resonance spectrum (CDCl$_3$+DMSO-d$_6$, δ, ppm): 1.52, 1.62 (6H, d), 2.45, 2.53 (6H, d), 4.33 (1H, s), 5.47 (1H, d), 5.83 (2H, m), 7.23–7.50 (8H, m), 8.53 (1H, d), 8.74 (1H, d)

EXAMPLE 6

D(−)-α-(8-Methoxycoumarin-3-carbonamido)benzylpenicillin

A mixture of 8-methoxycoumarin-3-carboxylic acid (1.54 g) and thionyl chloride (7 ml) was heated under reflux for one hour. After the excess thionyl chloride had been distilled off under reduced pressure, the resulting residue was suspended in acetone (10 ml). This solution was added dropwise to a solution of sodium ampicillin (2.6 g) in acetone-water (1:1) (20 ml) under stirring and cooling on ice, during which time the pH was maintained in the range of from 7 to 9 with a dilute aqueous solution of sodium hydroxide. After the addition was completed, the mixture was stirred for thirty minutes, ethyl acetate (50 ml) was added, and the pH was adjusted to 2 with a dilute aqueous solution of hydrochloric acid. The organic layer was separated, washed successively with a dilute hydrochloric acid, a saturated solution of sodium chloride and water, and then dried over anhydrous sodium sulfate. After removal of the solvent under reduced pressure the resulting residue was treated with ethyl acetate, yielding D(−)-α-(8-methoxycoumarin-3-carbonamido)benzylpenicillin, m.p. 163°–4° C. (dec.). The yield was 1.35 g.
Elemental analysis ($C_{27}H_{25}N_3O_8S$):

|  | C | H | N |
|---|---|---|---|
| Observed | 56.42 | 4.50 | 7.88 |
| Calculated | 56.57 | 4.57 | 7.61 |

Infrared spectrum (KBr, cm$^{-1}$): 3250 (NH), 1770 (β-lactam), 1710 (carboxylic acid), 1640 (amide), 1720, 1640, 1570 (lactone)
Nuclear magnetic resonance spectrum (CDCl$_3$+DMSO-d$_6$, δ, ppm): 1.49, 1.55 (6H, d), 3.96 (3H, s, —OCH$_3$), 4.28 (1H, s), 5.4 (1H, d), 5.53 (1H, q), 5.90 (1H, d), 7.25–7.50 (8H, m), 8.45 (1H, d), 8.78 (1H, s), 9.88 (1H, d)

EXAMPLE 7

D(−)-α-(6-Methoxycoumarin-3-carbonamido)benzylpenicillin

D(−)-α-(6-methoxycoumarin-3-carbonamido)benzylpenicillin, 0.27 g, m.p. 164°–8° C. (dec.), was obtained from 6-methoxycoumarin-3-carboxylic acid (0.22 g) in the similar manner as in example 6.
Elemental analysis ($C_{27}H_{25}N_3O_8S$):

|  | C | H | N |
|---|---|---|---|
| Observed | 56.55 | 4.60 | 7.55 |
| Calculated | 56.57 | 4.57 | 7.61 |

Infrared spectrum (KBr, cm$^{-1}$): 3450, 3300 (NH, OH), 1770 (β-lactam), 1700 (carboxylic acid), 1650 (amide), 1700, 1620, 1570 (lactone)
Nuclear magnetic resonance spectrum (CDCl$_3$+DMSO-d$_6$, δ, ppm): 1.47, 1.55 (6H, d), 3.85 (3H, s), 4.27 (1H, s), 5.40 (1H, d), 5.80 (2H, m), 7.23 (8H, m), 8.77 (1H, d), 9.00 (1H, d), 9.80 (1H, d)

EXAMPLE 8

D(−)-α-(7-Methoxycoumarin-3-carbonamido)benzylpenicillin

D(−)-α-(7-methoxycoumarin-3-carbonamido)benzylpenicillin, 0.19 g, m.p. 160°–3° C. (dec.), was obtained from 7-methoxycoumarin-3-carboxylic acid (0.22 g) in the similar manner as in example 6.
Elemental analysis ($C_{27}H_{25}N_3O_8S$):

|  | C | H | N |
|---|---|---|---|
| Observed | 56.62 | 4.35 | 7.33 |
| Calculated | 56.57 | 4.57 | 7.61 |

Infrared spectrum (KBr, cm$^{-1}$): 3450, 3350 (NH, OH), 1780 (β-lactam), 1710 (carboxylic acid), 1650 (amide), 1710, 1615, 1550 (lactone)
Nuclear magnetic resonance spectrum (DMSO-d$_6$, δ, ppm): 1.42 (6H, s), 3.82 (3H, s), 4.17 (1H, s), 5.3–5.7 (3H, m), 7.2–7.5 (8H, m), 8.67 (1H, s), 9.66 (1H, d)

EXAMPLE 9

D(−)-α-(6-Acetoxycoumarin-3-carbonamido)benzylpenicillin

D(−)-α-(6-acetoxycoumarin-3-carbonamido)benzylpenicillin (0.2 g), m.p. 135°–8° C. (dec.), was obtained from 6-acetoxycoumarin-3-carboxylic acid (0.248 g) in the similar manner as in example 6.
Elemental analysis ($C_{28}H_{25}N_3O_9S$):

|  | C | H | N |
|---|---|---|---|
| Observed | 57.72 | 3.99 | 7.55 |
| Calculated | 57.98 | 4.34 | 7.25 |

Infrared spectrum (cm$^{-1}$): 3450, 3300 (NH, OH), 1760 (β-lactam), 1720, 1610, 1570 (lactone), 1700 (carboxylic acid), 1650 (amide)
Nuclear magnetic resonance spectrum (CDCl$_3$αDMSO-d$_6$, δ, ppm): 1.51, 1.56 (6H, d), 2.35

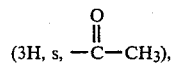

4.33 (1H, s), 5.5 (1H, d), 5.6–5.9 (2H, m), 7.3–7.5 (8H, m), 7.85 (1H, d), 8.88 (1H, s), 9.90 (1H, d)

EXAMPLE 10

D(−)-α-(6-Hydroxycoumarin-3-carbonamido)benzylpenicillin

6-Hydroxycoumarin-3-carboxylic acid (0.206 g), previously suspended in anhydrous methylene chloride (8 ml), was dissolved by addition of triethylamine (0.101 g). Ethyl chlorocarbonate (0.110 g) was added to the solution at −15° C. and the mixture was stirred at temperatures between −15° C. and −20° C. for thirty minutes. Separately, amplicillin trihydrate (0.403 g) was suspended in methylene chloride (6 ml). To this suspension was added triethylamine (0.35 g) and magnesium sulfate (0.3 g) successively, and the mixture was stirred for thirty minutes. After removal of the magnesium sulfate, the solution of mixed acid anhydride in methylene chloride obtained above was added dropwise to the filtrate at temperatures from −15° C. and −20° C. After the addition was completed the mixture was stirred for thirty minutes, during which the temperature was allowed to rise to room temperature. After the completion of the reaction, 50 ml ethyl acetate and 20 ml water were added, and the pH of the mixture was adjusted to 2 with a 1 N hydrochloric acid solution. The organic layer was separated, washed twice with 15 ml of a 1 N hydrochloric acid solution and then twice with 15 ml of a saturated solution of sodium chloride successively, and dried over anhydrous sodium sulfate. After distilling off the solvent, the resulting residue was treated with ether, affording D(−)-α-(6-hydroxycoumarin-3-carbonamido)benzylpenicillin (0.137 g), melting at 161°–3° C. (dec.).

Elemental analysis ($C_{26}H_{23}N_3O_8S$):

| | C | H | N |
|---|---|---|---|
| Observed | 57.55 | 4.00 | 7.42 |
| Calculated | 58.04 | 4.31 | 7.81 |

Infrared spectrum (KBr, cm$^{-1}$): 3300 (NH, OH), 1760 (β-lactam), 1720 (carboxylic acid), 1650 (amide), 1720, 1650, 1570 (lactone)

Nuclear magnetic resonance spectrum (CDCl$_3$+DMSO-d$_6$, δ, ppm): 1.56, 1.62 (6H, d), 4.34 (1H, s), 5.45 (2H, m), 6.0 (1H, d), 7.45–7.55 (8H, m), 7.77 (1H, s), 8.88 (1H, s), 9.81 (1H, d)

EXAMPLE 11

D(−)-α-(7-Hydroxycoumarin-3-carbonamido)benzylpenicillin

D(−)-α-(7-Hydroxycoumarin-3-carbonamido)benzylpenicillin (0.193 g), m.p. 145°–50° C. (dec.), was obtained from 7-hydroxycoumarin-3-carboxylic acid (0.206 g) in the same manner as in example 10.

Elemental analysis ($C_{26}H_{23}N_3O_8S$):

| | C | H | N |
|---|---|---|---|
| Observed | 57.63 | 4.10 | 7.50 |
| Calculated | 58.04 | 4.31 | 7.81 |

Infrared spectrum (KBr, cm$^{-1}$): 3400 (NH, OH), 1770 (β-lactam), 1745, 1620, 1570 (lactone), 1680 (carboxylic acid, amide)

Nuclear magnetic resonance spectrum (CDCl$_3$+DMSO-d$_6$, δ, ppm): 1.43, 1.57 (6H, d), 4.25 (1H, s), 4.93 (1H, d), 5.40 (1H, m), 5.85 (1H, d), 7.15–7.80 (8H, m), 8.25 (1H, d), 8.80 (1H, s), 9.75 (1H, d)

EXAMPLE 12

D(−)-α-(7-Acetoxycoumarin-3-carbonamido)benzylpenicillin

D(−)-α-(7-Acetoxycoumarin-3-carbonamido)benzylpenicillin (0.095 g), m.p. 155°–9° C. (dec.), was obtained from 7-acetoxycoumarin-3-carboxylic acid (0.052 g) in the same manner as in example 8.

Elemental analysis ($C_{28}H_{25}N_3O_9S$):

| | C | H | N |
|---|---|---|---|
| Observed | 57.65 | 4.20 | 7.01 |
| Calculated | 57.98 | 4.31 | 7.25 |

Infrared spectrum (cm$^{-1}$): 3450, 3300 (OH, NH), 1760 (β-lactam), 1705, 1610, 1565 (lactone), 1700 (carboxylic acid), 1650 (amide)

Nuclear magnetic resonance spectrum: 1.42, 1.53 (6H, d), 2.30

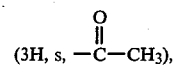

4.20 (1H, s), 5.40 (2H, m), 5.85 (1H, d), 7.1–7.6 (8H, m), 8.76 (1H, s), 8.69 (1H, d)

EXAMPLE 13

D(−)-α-(6-Nitrocoumarin-3-carbonamido)benzylpenicillin

D(−)-α-(6-Nitrocoumarin-3-carbonamido)benzylpenicillin (0.138 g), m.p. 177°–9° C. (dec.), was obtained from the acid chloride prepared from 6-nitrocoumarin-3-carboxylic acid (0.235 g) and thionyl chloride (1 ml) in the similar manner as in example 1.

Elemental analysis ($C_{26}H_{22}N_4O_9S$):

| | C | H | N |
|---|---|---|---|
| Observed | 54.82 | 3.60 | 9.97 |
| Calculated | 54.98 | 3.90 | 9.86 |

Infrared spectrum (KBr, cm$^{-1}$): 3250 (NH, OH), 1770 (β-lactam), 1720 (carboxylic acid), 1660 (amide), 1720, 1615, 1565 (lactone), 1520 (nitro)

Nuclear magnetic resonance spectrum (CDCl$_3$+DMSO-d$_6$, δ, ppm): 1.45, 1.52 (6H, d), 4.2 (1H, s), 5.70 (1H, d), 6.00 (2H, m), 7.2–7.5 (8H, m), 8.4 (1H, d), 8.93 (1H, s), 8.70 (1H, d)

EXAMPLE 14

D(−)-α-(8-Methoxycarbonylcoumarin-3-carbonamido)benzylpenicillin

D(−)-α-(8-Methoxycarbonylcoumarin-3-carbonamido)benzylpenicillin (0.068 g), m.p. 159°–163° C. (dec.), was obtained in the similar manner as in example 1 from the acid chloride prepared by heating 8-methoxycarbonylcoumarin-3-carboxylic acid (0.252 g) and thionyl chloride (1 ml) under reflux for one hour.

Elemental analysis ($C_{28}H_{25}N_3O_9S$):

|  | C | H | N |
|---|---|---|---|
| Observed | 57.66 | 4.23 | 6.87 |
| Calculated | 57.98 | 4.34 | 7.25 |

Infrared spectrum (KBr, cm$^{-1}$): 3450, 3350 (NH, OH), 1780 (β-lactam), 1700 (carboxylic acid), 1660 (amide), 1730, 1610, 1580 (lactone)

Nuclear magnetic resonance spectrum (CDCl$_3$+DMSO-d$_6$, δ, ppm): 1.48, 1.57 (6H, d), 3.97 (3H, s, —CO$_2$CH$_3$), 4.25 (1H, s), 4.93 (1H, d), 7.2–7.6 (8H, m), 7.93 (1H, d), 8.8 (1H, s), 9.73 (1H, d)

EXAMPLE 15

D(−)-α-(8-Methylcoumarin-3-carbonamido)benzylpenicillin

A mixture of 8-methylcoumarin-3-carboxylic acid (0.2 g), thionyl chloride (1 ml), and benzene (1 ml) was heated under reflux for fourty five minutes. After distilling off the solvent and excess thionyl chloride, the residue was dissolved in 3 ml acetone. This solution was added dropwise under stirring and cooling on ice to a solution of ampicillin trihydrate (0.5 g) in acetone-water (1:1) (5 ml), which was previously adjusted to pH 8.0 with a dilute aqueous solution of caustic soda. During addition the pH was maintained in the range of from 7 to 9 with a dilute aqueous solution of caustic soda. After the completion of the addition, the mixture was stirred for one hour and treated in the same manner as in example 1, yielding D(−)-α-(8-methylcoumarin-3-carbonamido)benzylpenicillin (0.096 g), m.p. 225°–9° C. (dec.).

Elemental analysis ($C_{27}H_{25}N_3O_7S$):

|  | C | H | N |
|---|---|---|---|
| Observed | 59.98 | 4.65 | 7.58 |
| Calculated | 60.50 | 4.70 | 7.84 |

Infrared spectrum (KBr, cm$^{-1}$): 3400, 3300 (NH, OH), 1770 (β-lactam), 1705 (carboxylic acid), 1720, 1610, 1585 (lactone), 1655 (amide)

Nuclear magnetic resonance spectrum: 1.57 (6H, s), 1.68 (3H, s, —CH$_3$), 4.35 (1H, s), 5.50 (3H, m), 7.47 (8H, m), 8.88 (1H, s), 9.82 (1H, d)

EXAMPLE 16

D(−)-α-(Coumarin-3-carbonamido)-p-hydroxybenzylpenicillin

A mixture of coumarin-3-carboxylic acid (0.19 g) and thionyl chloride (0.5 ml) was heated under reflux for one hour. After distilling off the excess thionyl chloride under reduced pressure, the residue was suspended in acetone. This suspension was added dropwise under stirring and cooling on ice to a solution of amoxycillin (0.419 g) in water (5 ml), which was previously adjusted to pH 8 with a dilute aqueous caustic soda solution. During addition the pH of the reaction mixture was maintained in the range of 7–9 with a dilute aqueous solution of caustic soda. After the completion of the addition, the mixture was stirred for one hour, 20 ml ethyl acetate was added, and the pH of the mixture was adjusted to 2 with a 1 N aqueous hydrochloric acid. The organic layer was separated, washed twice with 10 ml of a 1 N aqueous hydrochloric acid and then twice with 10 ml of a saturated sodium chloride solution, and dried over anhydrous sodium sulfate. Removing the solvent under reduced pressure and treating the residue with benzene afforded D(−)-α-(coumarin-3-carbonamido)-p-hydroxybenzylpenicillin (0.275 g), m.p. 172°–3° C. (dec.).

Elemental analysis ($C_{26}H_{23}N_3O_8S$):

|  | C | H | N |
|---|---|---|---|
| Observed | 57.59 | 3.92 | 7.62 |
| Calculated | 58.04 | 4.31 | 7.81 |

Infrared spectrum (KBr, cm$^{-1}$): 3300 (NH, OH), 1770 (β-lactam), 1710 (carboxylic acid), 1660 (amide), 1725, 1615, 1570 (lactone)

Nuclear magnetic resonance spectrum (CDCl$_3$+DMSO-d$_6$, β, ppm): 1.50, 1.56 (6H, d), 4.30 (1H, s), 5.43 (1H), 5.5–5.8 (2H, m), 6.7 (2H, d), 7.2–7.6 (6H, m), 8.17 (1H, d), 8.83 (1H, s), 9.73 (1H, d)

EXAMPLE 17

D(−)-α-(6-Acetoxycoumarin-3-carbonamido)-p-hydroxybenzylpenicillin

D(−)-α-(6-Acetoxycoumarin-3-carbonamido)-p-hydroxybenzylpenicillin (0.10 g), m.p. 163°–8° C. (dec.), was obtained from 6-acetoxycoumarin-3-carboxylic acid (0.232 g) in the similar manner as in example 16.

Elemental analysis ($C_{28}H_{25}N_3O_{10}S$):

|  | C | H | N |
|---|---|---|---|
| Observed | 56.03 | 4.35 | 6.88 |
| Calculated | 56.42 | 4.23 | 7.05 |

Infrared spectrum (KBr, cm$^{-1}$): 3350 (NH, OH), 1760 (β-lactam), 1710 (carboxylic acid), 1760 (amide), 1730, 1620, 1580 (lactone), 1210 (OH)

Nuclear magnetic resonance spectrum (CDCl$_3$+DMSO-d$_6$, δ, ppm): 1.52, 1.62 (6H, d), 2.27 (3H, s), 5.43 (1H, s), 6.17–6.6 (3H, m), 6.77(2H, d), 7.13–7.5 (5H, m), 8.77 (1H, s), 9.63 (1H, d)

EXAMPLE 18

D(−)-α-(8-Methoxycoumarin-3-carbonamido)-p-hydroxylbenzylpenicillin

A mixture of 8-methoxycoumarin-3-carboxylic acid (0.66 g) and thionyl chloride (2.5 ml) was heated under reflux for one and half hours. Distilling off the excess thionyl chloride in vacuo gave 8-methoxycoumarin-3-carboxylic acid chloride. Reaction of this product with amoxycillin, 1.257 g, in the same manner as in example 16, yielded D(−)-α-(8-methoxycoumarin-3-carbonamido)-p-hydroxybenzylpenicillin (0.95 g), melting at 187°–9° C. (dec.).

Elemental analysis ($C_{27}H_{25}N_3O_9S$):

|  | C | H | N |
|---|---|---|---|
| Observed | 56.62 | 4.30 | 7.29 |
| Calculated | 57.09 | 4.44 | 7.40 |

Infrared spectrum (KBr, cm$^{-1}$): 3400 (NH,OH), 1780 ($\beta$-lactam), 1720 (carboxylic acid), 1655 (amide), 1720, 1620, 1585 (lactone)

Nuclear magnetic resonance spectrum (DMSO-d$_6$, $\delta$, ppm): 1.50, 1.63 (6H, d), 4.00 (3H, s), 4.25 (1H, s), 5.41 (2H, m), 5.80 (1H, d), 6.77 (2H, d), 7.27 (5H, m), 7.83 (1H, s), 8.80 (1H, s), 9.63 (1H, d)

EXAMPLE 19

D(−)-$\alpha$-(8-Ethoxycoumarin-3-carbonamido)benzylpenicillin

D(−)-$\alpha$-(8-Ethoxycoumarin-3-carbonamido)benzylpenicillin (0.164 g), m.p. 150°–5° C. (dec.), was obtained from 8-ethoxycoumarin-3-carboxylic acid (0.234 g), in the similar manner as in example 1.

Elemental analysis (C$_{28}$H$_{27}$N$_3$O$_8$S):

|  | C | H | N |
|---|---|---|---|
| Observed | 58.96 | 4.90 | 7.27 |
| Calculated | 59.41 | 4.81 | 7.42 |

Infrared spectrum (KBr, cm$^{-1}$): 3450, 3350 (NH, OH), 1780 ($\beta$-lactam), 1710, 1610, 1580 (lactone), 1690 (carboxylic acid), 1650 (amide)

Nuclear magnetic resonance spectrum (CDCl$_3$+DMSO-d$_6$, $\delta$, ppm): 1.17 (3H, t, —OCH$_2$CH$_3$), 1.47 (6H, s), 3.47 (2H, q, —OCH$_2$CH$_3$), 4.10 (1H, d), 4.60 (1H, d), 5.5 (2H, m), 7.15–7.5 (8H, m), 8.80 (1H, s), 9.87 (1H, d)

EXAMPLE 20

D(−)-$\alpha$-(6-Acetylaminocoumarin-3-carbonamido)benzylpenicillin

D(−)-$\alpha$-(6-Acetylaminocoumarin-3-carbonamido)-benzylpenicillin (0.145 g), m.p. 181°–4° C. (dec.), was obtained from 6-acetylaminocoumarin-3-carboxylic acid (0.247 g) through a mixed anhydride in the similar manner as in example 10.

Elemental analysis (C$_{28}$H$_{26}$N$_4$O$_8$S):

|  | C | H | N |
|---|---|---|---|
| Observed | 57.55 | 4.45 | 9.52 |
| Calculated | 58.08 | 4.53 | 9.66 |

Infrared spectrum (KBr, cm$^{-1}$): 3500, 3350 (NH, OH), 1780 ($\beta$-lactam), 1720, 1620, 1570 (lactone), 1700–1660 (carboxylic acid, amide)

Nuclear magnetic resonance spectrum (CDCl$_3$+DMSO-d$_6$, $\delta$, ppm): 1.37, 1.48 (6H, d), 2.03 (3H, s, —NHCOCH$_3$), 4.17 (1H, s), 5.33 (2H, m), 5.83 (1H, d), 7.25–8.1 (8H, m), 8.73 (1H, s), 9.13 (1H, d), 9.7 (1H, d), 10.0 (1H, s)

EXAMPLE 21

D-$\alpha$-(8-Acetoxycoumarin-3-carbonamido)benzylpenicillin

A mixture of 8-acetoxycoumarin-3-carboxylic acid (0.248 g) and thionyl chloride (1.5 ml) was heated under reflux for two hours. After distilling off the excess thionyl chloride, the residue was dissolved in 10 ml acetone. This solution was added under stirring and cooling on ice to a solution of sodium ampicillin (0.403 g) in 5 ml acetone-water (1:1), during which time the pH was maintained in the range of 7–9 with a dilute aqueous caustic soda solution. Stirring was continued for thirty minutes after the end of the addition, ethyl acetate (10 ml) was added, and the pH was adjusted to 2 with a dilute aqueous hydrochloric acid. The ethyl acetate layer was separated, washed successively with 1 N aqueous hydrochloric acid, a saturated aqueous solution of sodium chloride and water, and then dried over anhydrous sodium sulfate. Distilling off the solvent in vacuo and treating the residue with ether yielded D-$\alpha$-(8-acetoxycoumarin-3-carbonamido)benzylpenicillin (0.140 g), m.p. 159°–160° C. (dec.).

Elemental analysis (C$_{28}$H$_{25}$N$_3$O$_9$S):

|  | C | H | N |
|---|---|---|---|
| Observed | 57.65 | 4.25 | 6.90 |
| Calculated | 57.98 | 4.34 | 7.25 |

Infrared spectrum (cm$^{-1}$): 3500, 3400 (NH, OH), 1780 ($\beta$-lactam), 1730 (carbonyl), 1655 (amide), 1620, 1585 (lactone)

Nuclear magnetic resonance spectrum (CDCl$_3$+DMSO-d$_6$, $\delta$, ppm): 1.52, 1.65 (6H, 2CH$_3$), 2.47 (3H, s, —COCH$_3$), 4.28 (1H, s), 5.4–5.7 (2H, m), 6.0 (1H, d), 7.27–7.83 (8H, m, aromatic nucleus), 8.93 (1H, s), 9.37 (1H, d), 9.63 (1H, d)

EXAMPLE 22

D-$\alpha$-(5,7-Dimethoxycoumarin-3-carbonamido)benzylpenicillin

D-$\alpha$-(5,7-dimethoxy-3-carbonamido)benzylpenicillin (0.315 g), m.p. 165°–7° C. (dec.), was obtained from 5,7-dimethoxycoumarin-3-carboxylic acid (0.248 g) in the similar manner as in example 21.

Elemental analysis (C$_{28}$H$_{27}$N$_3$O$_9$S):

|  | C | H | N |
|---|---|---|---|
| Observed | 57.15 | 4.53 | 6.94 |
| Calculated | 57.78 | 4.68 | 7.22 |

Infrared spectrum (cm$^{-1}$): 3500, 3400 (NH, OH), 1790 ($\beta$-lactam), 1630 (amide), 1715, 1610, 1570 (lactone)

Nuclear magnetic resonance spectrum (CDCl$_3$+DMSO-d$_6$, $\delta$, ppm): 1.42, 1.55 (6H, 2CH$_3$), 3.81 (6H, 2CH$_3$), 4.17 (1H, s), 5.23–5.6 (2H, m), 5.93 (1H, d), 7.15–7.5 (7H, m), 7.9 (1H, s), 9.13 (1H, d), 9.53 (1H, d)

EXAMPLE 23

D-$\alpha$-(6-Ethoxycoumarin-3-carbonamido)benzylpenicillin

D-$\alpha$-(6-Ethoxycoumarin-3-carbonamido)benzylpenicillin (0.619 g), m.p. 176°–8° C. (dec.), was obtained from 6-ethoxycoumarin-3-carboxylic acid (0.351 g) in the similar manner as in example 21.

Elemental analysis (C$_{28}$H$_{27}$N$_3$O$_8$S):

|  | C | H | N |
|---|---|---|---|
| Observed | 59.12 | 4.75 | 7.05 |

| | C | H | N |
|---|---|---|---|
| Calculated | 59.41 | 4.81 | 7.42 |

Infrared spectrum (cm$^{-1}$): 3350 (NH, OH), 1790 ($\beta$-lactam), 1655 (amide), 1710, 1620, 1580 (lactone)

Nuclear magnetic resonance spectrum (CDCl$_3$+DMSO-d$_6$, $\delta$, ppm): 1.15 (3H, t), 1.47, 1.50 (6H, 2CH$_3$), 3.43 (2H, q), 4.23 (1H, s), 5.33–5.53 (2H, m), 5.93 (1H, d), 7.16–7.90 (9H, m), 9.87 (1H, d)

EXAMPLE 24

D-$\alpha$-(5-Methoxycoumarin-3-carbonamido)benzylpenicillin

D-$\alpha$-(5-Methoxycoumarin-3-carbonamido)benzylpenicillin (0.03 g), m.p. 131°–2° C. (dec.), was obtained from 5-methoxycoumarin-3-carboxylic acid (0.043 g) in the similar manner as in example 21.

Elemental analysis (C$_{27}$H$_{25}$N$_3$O$_8$S):

| | C | H | N |
|---|---|---|---|
| Observed | 56.08 | 4.23 | 7.35 |
| Calculated | 56.57 | 4.57 | 7.61 |

Infrared spectrum (KBr, cm$^{-1}$): 3450 (NH, OH), 1770 ($\beta$-lactam), 1670 (amide)

EXAMPLE 25

D-$\alpha$-(8-Ethoxycoumarin-3-carbonamido)-p-hydroxybenzylpenicillin

A mixture of 8-ethoxycoumarin-3-carboxylic acid (0.234 g) and thionyl chloride (1 ml) was heated under reflux for one and half hours. After distilling off the excess thionyl chloride in vacuo, the residue was dissolved in 5 ml acetone. This solution was added dropwise under stirring and cooling on ice to a suspension of amoxycillin (0.419 g) in water-acetone (1:1) (5 ml) adjusted to pH 8 with a dilute aqueous caustic soda, during which time the pH of the mixture was maintained in the range of 8–9 with a 1 N aqueous caustic soda solution. After the end of the addition of the acetone solution, the mixture was stirred for thirty minutes, 30 ml ethyl acetate was added, and the pH was adjusted to 2 with a dilute aqueous hydrochloric acid. The ethyl acetate layer was separated, washed successively with a 1 N aqueous hydrochloric acid, a saturated sodium chloride solution and water, and dried over anhydrous sodium sulfate. Distilling off the solvent and treating the residue with ether yielded D-$\alpha$-(8-ethoxycoumarin-3-carbonamido)-p-hydroxybenzylpenicillin, m.p. 185°–7° C. (dec.).

Elemental analysis (C$_{28}$H$_{27}$N$_3$O$_9$S):

| | C | H | N |
|---|---|---|---|
| Observed | 57.53 | 4.53 | 7.05 |
| Calculated | 57.78 | 4.68 | 7.22 |

Infrared spectrum (KBr, cm$^{-1}$): 3400 (NH, OH), 1780 ($\beta$-lactam), 1650 (amide), 1720, 1620, 1580 (lactone)

EXAMPLE 26

D(−)-$\alpha$-(8-Hydroxycoumarin-3-carbonamido)benzylpenicillin

A solution of 8-hydroxycoumarin-3-carboxylic acid (2.06 g) in 10 ml thionyl chloride was heated under reflux for three hours, and 8-hydroxycoumarin-3-carboxylic acid chloride was obtained by distilling off the excess thionyl chloride. This was added in small portions to a methylene chloride solution (100 ml) containing ampicillin trihydrate (4.1 g) and triethylamine (3.5 ml) over a period of forty minutes under stirring and cooling on ice.

After the addition was completed, the mixture was stirred under cooling on ice for one hour, water (80 ml) and ethyl acetate (150 ml) were added, and the mixture was adjusted to pH 2.0 with a 1 N aqueous hydrochloric acid.

The organic layer was separated, washed thrice with a 1 N aqueous hydrochloric acid solution (each 30 ml) and twice with water (each 30 ml) and then dried over anhydrous magnesium sulfate. Distilling of the solvent under reduced pressure and purifying the residue with ethyl acetate-diethyl ether yielded D(−)-$\alpha$-(8-hydroxycoumarin-3-carbonamido)benzylpenicillin (2.87 g), m.p. 195°–200° C. (dec.).

Elemental analysis (C$_{26}$H$_{23}$N$_3$O$_8$):

| | C | H | N |
|---|---|---|---|
| Observed | 57.83 | 4.25 | 7.77 |
| Calculated | 53.04 | 4.31 | 7.81 |

Infrared spectrum (KBr, cm$^{-1}$): 3350 (NH, OH), 1780 ($\beta$-lactam), 1720, 1650, 1580 (lactone), 1610 (carboxylic amide).

EXAMPLE 27

D(−)-$\alpha$-(coumarin-3-carbonamido)benzylpenicillin

A mixture of coumarin-3-carboxylic acid (0.57 g) and thionyl chloride (3 ml) was heated under reflux for one hour. Distilling off the excess thionyl chloride under reduced pressure yielded the acid chloride. Phenylglycine (0.453 g) was suspended in 5 ml acetone-water (1:1) and the pH was adjusted to 8 with a dilute aqueous caustic soda solution. To this was added under cooling on ice a solution of the acid chloride obtained above in acetone (5 ml), during which time the pH of the reaction mixture was maintained in the range of 7–9 with a dilute aqueous caustic soda solution. After the completion of the addition, the mixture was stirred for thirty minutes and the insoluble substances were filtered off. A 1 N aqueous hydrochloric acid was added to the filtrate and N-(coumarin-3-carbonyl)phenylglycine (0.75 g) precipitated was collected. To this product (0.323 g) was added 1 ml thionyl chloride and the mixture was heated under reflux for one hour. Distilling off the excess thionyl chloride yielded the acid chloride. Separately, triethylamine (0.202 g) was added to a suspension of 6-aminopenicillanic acid (0.216 g) in methylene chloride (5 ml), which gave a clear solution after stirring for two hours at room temperature. To this solution was added under cooling on ice a suspension of the acid chloride obtained above in 5 ml methylene chloride, and stirring was continued for additional one and half hours. Ethyl acetate (50 ml) and water (50 ml) were added, and the organic layer separated was washed

| | Staphylococcus aureus 209-p (1) | Staphylococcus aureus 1248 (2) | Bacillus subtilis (3) | Salmonella typhimurium G-20 (4) | Escherichia Coli NIHJ JC-2 (5) | Klebsiella neumoniae ATCC10031 (6) | Enterobacter cloacae 147 (7) | Enterobacter cloacae IFO12937 (8) | Morganella var. G-2 (9) | Rettgerella var. Tid-21 (10) | Serratia G-18 (11) | Pseudomonas aeruginosa IFO-3080 (12) | Pseudomonas aeruginosa 0-37 (13) | Pseudomonas aeruginosa Tid-53 (14) | Pseudomonas aeruginosa GN-315 (15) | Pseudomonas aeruginosa 130 (16) |
|---|---|---|---|---|---|---|---|---|---|---|---|---|---|---|---|---|
| 1 | <0.4 | 1.56 | <0.4 | <0.4 | <0.4 | <0.4 | 3.13 | 6.25 | 3.13 | 1.56 | 12.5 | <0.4 | 12.5 | 3.13 | 1.56 | <0.4 |
| 2 | <0.4 | 1.56 | <0.4 | <0.4 | <0.4 | 1.56 | 25 | 25 | 12.5 | 12.5 | 50 | 3.13 | 50 | 25 | 25 | 6.25 |
| 3 | <0.4 | 1.56 | <0.4 | <0.4 | <0.4 | 1.56 | 3.13 | 25 | 6.25 | 6.25 | 25 | 1.56 | 25 | 6.25 | 6.25 | 1.56 |
| 4 | 1.56 | 50 | 1.56 | 3.13 | <0.4 | 3.13 | 50 | 200 | 25 | 100 | 100 | 50 | 200 | 200 | 200 | 50 |
| 5 | <0.4 | 1.56 | <0.4 | <0.4 | <0.4 | 0.8 | 100 | 50 | 25 | 25 | 50 | 12.5 | 200 | 50 | 50 | 12.5 |
| 6 | <0.4 | 0.8 | <0.4 | <0.4 | <0.4 | 0.8 | 3.13 | 6.25 | 0.8 | 6.25 | 6.25 | 0.8 | 12.5 | 6.25 | 3.13 | 1.56 |
| 7 | <0.4 | 1.56 | <0.4 | <0.4 | <0.4 | <0.4 | 3.13 | 3.13 | 6.25 | 6.25 | 12.5 | 1.56 | 25 | 3.13 | 3.13 | 1.56 |
| 8 | <0.4 | <0.4 | <0.4 | <0.4 | <0.4 | <0.4 | 1.56 | 25 | 3.13 | 3.13 | 12.5 | 1.56 | 25 | 3.13 | 3.13 | 1.56 |
| 9 | <0.4 | 1.56 | <0.4 | <0.4 | <0.4 | 0.8 | 3.13 | 25 | 6.25 | 6.25 | 25 | 0.8 | 25 | 6.25 | 6.25 | 3.13 |
| 10 | <0.4 | 6.25 | <0.4 | <0.4 | <0.4 | 12.5 | 12.5 | 50 | 50 | 25 | 200 | 1.56 | 100 | 25 | 12.5 | <0.4 |
| 11 | <0.4 | 3.13 | <0.4 | <0.4 | <0.4 | 12.5 | 12.5 | 100 | 25 | 50 | 100 | 3.13 | 50 | 25 | 25 | 3.13 |
| 12 | <0.4 | 6.25 | <0.4 | <0.4 | <0.4 | 12.5 | 25 | 12.5 | 6.25 | 12.5 | 50 | 1.56 | 100 | 25 | 12.5 | 6.25 |
| 13 | <0.4 | 3.13 | <0.4 | <0.4 | <0.4 | 1.56 | 25 | 6.25 | 1.56 | 50 | 12.5 | 6.25 | 100 | 25 | 12.5 | 6.25 |
| 14 | <0.4 | 6.25 | <0.4 | <0.4 | <0.4 | 6.25 | 200 | 100 | 100 | 12.5 | 200 | 6.25 | 200 | 25 | 12.5 | 3.13 |
| 15 | <0.4 | 3.13 | <0.4 | <0.4 | <0.4 | 3.13 | 6.25 | 25 | 12.5 | 50 | 50 | 12.5 | 200 | 100 | 200 | 3.13 |
| 16 | <0.4 | 1.56 | <0.4 | <0.4 | <0.4 | 0.8 | 12.5 | 12.5 | 12.5 | 1.56 | 50 | 0.8 | 25 | 6.25 | 3.13 | 25 |
| 17 | <0.4 | 3.13 | <0.4 | <0.4 | <0.4 | <0.4 | 3.13 | 3.13 | 3.13 | 3.13 | 6.25 | 0.8 | 12.5 | 3.13 | 3.13 | 1.56 |
| 18 | <0.4 | 1.56 | <0.4 | <0.4 | <0.4 | 0.8 | 12.5 | 12.5 | 3.13 | 3.13 | 12.5 | 1.56 | 12.5 | 3.13 | 3.13 | 1.56 |
| 19 | <0.4 | 3.13 | <0.4 | <0.4 | <0.4 | <0.4 | 3.13 | 3.13 | 6.25 | 6.25 | 50 | 3.13 | 50 | 3.13 | 6.25 | 1.56 |
| 20 | <0.4 | 3.13 | <0.4 | <0.4 | <0.4 | 1.56 | 6.25 | 6.25 | 6.25 | 1.56 | 6.25 | <0.4 | 50 | 6.25 | 6.25 | 1.56 |
| 21 | <0.4 | 3.13 | <0.4 | <0.4 | <0.4 | 0.8 | 12.5 | 6.25 | 1.56 | 1.56 | 12.5 | 1.56 | 50 | 12.5 | 6.25 | 0.8 |
| 22 | <0.4 | 3.13 | — | — | <0.4 | 1.56 | 1.56 | 50 | 50 | 25 | 100 | 0.8 | 50 | 6.25 | 6.25 | 3.13 |
| 23 | <0.4 | 3.13 | — | — | <0.4 | 6.25 | 1.56 | 6.25 | 3.13 | 3.13 | 25 | 0.8 | 12.5 | 3.13 | 3.13 | 1.56 |
| 24 | <0.4 | — | — | — | <0.4 | — | 1.56 | 6.25 | 3.13 | 1.56 | 25 | 0.8 | 12.5 | 3.13 | 3.13 | 1.56 |
| 26 | <0.4 | — | <0.4 | — | <0.4 | — | 3.13 | 12.5 | 1.56 | 1.56 | 12.5 | <0.4 | 50 | 6.25 | 1.56 | 1.56 |
| Ampicillin | <0.8 | <0.8 | <0.8 | <0.8 | <0.8 | 12.5 | 400 | — | 12.5 | 6.25 | 25 | 200 | >400 | >400 | >400 | >400 |
| Carbenicillin | <0.8 | 3.13 | <0.8 | <0.8 | <0.8 | 50 | 200 | — | 1.56 | 25 | 6.25 | 12.5 | >400 | 200 | 100 | 25 | twice with a 1 N aqueous hydrochloric acid solution, twice with a saturated aqueous sodium chloride solution, and twice with water (each 20 ml) in succession, and dried over anhydrous sodium sulfate. Distilling off the solvent and recrystallizing the residue with ethyl acetate afforded D(−)-α-(coumarin-3-carbonamido)-benzyl penicillin (0.362 g), melting at 172°–4° C. (dec.). The properties of the product thus obtained were exactly the same with that prepared by the method of example 1.

EXAMPLE 28

Sodium salt of D(−)-α-(coumarin-3-carbonamido)benzylpenicillin

A 50% solution of sodium 2-ethylhexanoic acid in n-butanol was added to a solution of D(−)-α-(coumarin-3-carbonamido)benzylpenicillin (1.04 g) in 80 ml ethyl acetate until no more crystals were separated out. The crystals were collected by filtration and dried over phosphorus pentoxide, yielding sodium salt of D(−)-α-(coumarin-3-carbonamido)benzylpenicillin, melting at 205°–7° C. (dec.). The yield was 0.81 g.

Infrared spectrum (KBr, cm$^{-1}$): 3400, 3300 (NH, OH), 1760 (β-lactam), 1610 (carboxylate), 1640 (amide), 1710, 1610, 1560 (lactone)

EXAMPLE 29

Bis(trimethylsilyl)-6-aminopenicillanic acid, 1.9 g, was obtained from 6-aminopenicillanic acid (2.16 g) and trimethylchlorosilane (0.36 g) by a well-known method. This compound, 0.36 g, was dissolved in 5 ml tetrahydrofuran, and 0.13 g of quinoline was added. To this solution was added under cooling 0.342 g of the acid chloride of N-(8-methoxycoumarin-3-carbonyl)-phenylglycine. After the reaction was completed, methylene chloride was distilled off in vacuo, water (20 ml) and ethyl acetate (20 ml) were added, and the pH was adjusted to 2 with a dilute aqueous hydrochloric acid. The organic layer was separated, extracted with a 3% aqueous solution of sodium acetate. The aqueous extract was washed with ethyl acetate and the pH was adjusted to 2 with a dilute aqueous hydrochloric acid. It was again extracted with ethyl acetate, and the extract was washed successively with a dilute aqueous hydrochloric acid and water, and dried over anhydrous sodium sulfate. Distilling off the solvent under reduced pressure and treating the residue with ether gave D(−)-α-(8-methoxycoumarin-3-carbonamido)-benzylpenicillin, 1.55 g, melting at 162°–4° C. (dec.).

The properties of the product thus obtained were exactly the same with that prepared by the method of example 1.

Results of bactericidal tests (MIC, r/ml) on the penicillin derivatives of this invention prepared in the above examples are shown in the following table.

Acute toxicity values [(LD$_{50}$), mouse] of some penicillin derivatives of this invention are illustrated in the following table.

| Compound (Example No.) | Oral | Intraabdominal |
|---|---|---|
| 1 | >4g/Kg | — |
| 6 | >4g/Kg | 2g/Kg |
| 9 | " | " |
| 18 | " | " |

Rates of protein fixation (human serum protein) of the penicillin derivatives of this invention are illustrated as follows:

| Compound (Example No.) | Rate of protein fixation (%) |
|---|---|
| 2 | 67 |
| 3 | 80 |
| 6 | 58 |
| 9 | 80 |
| 16 | 45 |

What is claimed is:

1. Novel penicillin derivatives of formula [I]

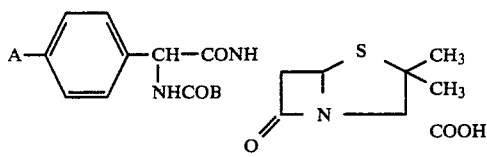

[I]

wherein A is hydrogen or hydroxyl, and B represents the coumarin nucleus of formula [III-a]

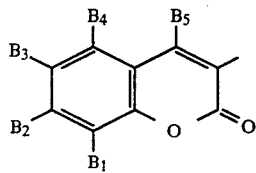

[III-a]

in which $B_1$, $B_2$, $B_3$, $B_4$ and $B_5$ are the same or different, and are selected from the group consisting of hydrogen, hydroxyl, thiol, acetyl, acetyloxy, amino, carboxyl, chloro, bromo, alkoxy of 1 to 4 carbon atoms, alkylmercapto of 1 to 4 carbon atoms, alkylamino of 1 to 8 carbon atoms, alkoxycarbonyl of 2 to 5 carbon atoms and nontoxic carboxylic salt, or nontoxic salts thereof.

2. Novel penicillin derivatives or nontoxic salts thereof as defined in claim 1, wherein at least three of the substituent groups $B_1$, $B_2$, $B_3$, $B_4$ and $B_5$ on the coumarin nucleus are hydrogen.

3. Novel penicillin derivatives or nontoxic salts thereof as defined in claim 1 or 2, wherein at least $B_1$ or $B_3$ of the substituent groups $B_1$, $B_2$, $B_3$, $B_4$ and $B_5$ are substituent groups other than hydrogen.

4. Bactericides containing a bactericidally effective amount of a novel penicillin derivative of formula [I]

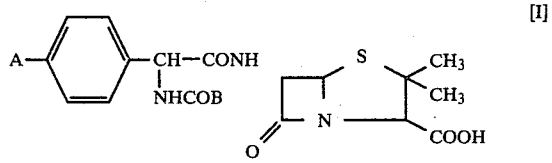

[I]

wherein A is hydrogen or hydroxyl, and B represents the coumarin nucleus of formula [III-a]

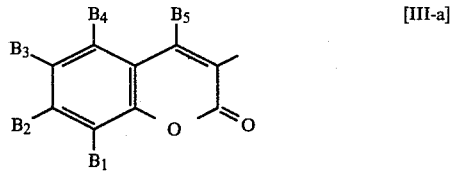

[III-a]

in which $B_1$, $B_2$, $B_3$, $B_4$ and $B_5$ are same or different, and are selected from the group consisting of hydrogen, hydroxyl, thiol, acetyl, acetyloxy, amino, carboxyl, chloro, bromo, alkoxy of 1 to 4 carbon atoms, alkylmercapto of 1 to 4 carbon atoms, alkylamino of 1 to 8 carbon atoms, alkoxycarbonyl of 2 to 5 carbon atoms and nontoxic carboxyl salt, or nontoxic salts thereof as a main ingredient and a nontoxic carrier.

5. Bactericides as defined in claim 4, wherein at least three of the substituent groups $B_1$, $B_2$, $B_3$, $B_4$ and $B_5$ on the coumarin nucleus are hydrogen.

6. Bactericides as defined in claim 4 or 5, wherein at least $B_1$ or $B_3$ are substituent groups other than hydrogen.

* * * * *